US010561357B2

(12) United States Patent
Patel et al.

(10) Patent No.: US 10,561,357 B2
(45) Date of Patent: Feb. 18, 2020

(54) AUTOMOTIVE DRIVER HEALTH MONITORING AND RESPONSE SYSTEM

(71) Applicant: STEERING SOLUTIONS IP HOLDING CORPORATION, Saginaw, MI (US)

(72) Inventors: Keyur R. Patel, Saginaw, MI (US); Patrik Ryne, Midland, MI (US); Joachim J. Klesing, Rochester, MI (US); Ashish C. Patel, Glen Allen, VA (US)

(73) Assignee: STEERING SOLUTIONS IP HOLDING CORPORATION, Saginaw, MI (US)

(*) Notice: Subject to any disclaimer, the term of this patent is extended or adjusted under 35 U.S.C. 154(b) by 0 days.

(21) Appl. No.: 15/720,283

(22) Filed: Sep. 29, 2017

(65) Prior Publication Data

US 2019/0099118 A1    Apr. 4, 2019

(51) Int. Cl.
| | | |
|---|---|---|
| *G08B 1/08* | (2006.01) | |
| *A61B 5/18* | (2006.01) | |
| *G07C 5/00* | (2006.01) | |
| *A61B 5/0205* | (2006.01) | |
| *A61B 5/00* | (2006.01) | |
| *G07C 5/08* | (2006.01) | |

(52) U.S. Cl.
CPC .............. *A61B 5/18* (2013.01); *A61B 5/0205* (2013.01); *A61B 5/6893* (2013.01); *A61B 5/746* (2013.01); *G07C 5/008* (2013.01); *G07C 5/0825* (2013.01); *A61B 5/681* (2013.01); *G07C 5/0808* (2013.01)

(58) Field of Classification Search
CPC ......... A61B 5/18; A61B 5/0205; A61B 5/681; G07C 5/008; G07C 5/0808
USPC .................................................... 340/573.1
See application file for complete search history.

(56) References Cited

U.S. PATENT DOCUMENTS

| | | | | |
|---|---|---|---|---|
| 8,874,301 | B1 * | 10/2014 | Rao ...................... | B60K 28/066 701/25 |
| 2010/0138149 | A1 * | 6/2010 | Ohta ...................... | G01C 21/26 701/533 |
| 2013/0009761 | A1 * | 1/2013 | Horseman ............ | A61B 5/6893 340/425.5 |
| 2014/0277896 | A1 * | 9/2014 | Lathrop .................. | B62D 1/04 701/23 |
| 2017/0012972 | A1 * | 1/2017 | Tanaka .................... | G06F 1/163 |
| 2017/0282856 | A1 * | 10/2017 | Riedel ..................... | B60R 25/25 |
| 2018/0004213 | A1 * | 1/2018 | Absmeier ......... | B60W 30/0956 |

* cited by examiner

*Primary Examiner* — Naomi J Small

(57) ABSTRACT

A method of monitoring a health condition of a driver of a vehicle includes activating a wearable device that is configured to provide a driver health signal and receiving the driver health signal at a controller. The method outputs for display a warning responsive to the driver health signal being indicative of at least one of an impending driver health event or current driver health event.

15 Claims, 2 Drawing Sheets

AUTOMOTIVE DRIVER HEALTH MONITORING AND RESPONSE SYSTEM

BACKGROUND

A vehicle may employ various sensors that detect a state of a driver while operating the vehicle. These various sensors may detect whether a driver is drowsy, paying attention, or even in the driver's seat. These various sensors are in communication with the vehicle warning system and may output an audible alarm or indicator should the sensor detect an unacceptable state of the driver. However, some of these existing sensors may be unable to detect health issues such as a heart attack or stroke.

Accordingly, it is desirable to provide a driver health monitoring system capable of detecting various health issues.

SUMMARY

According to an embodiment of the present disclosure, a steering assembly is provided. The steering assembly includes an advanced driver assistance system, a steering wheel, and a driver monitoring system. The advanced driver assistance system is configured to control a vehicle. The steering wheel is movable between a deployed position and a retracted position based on a state of the advanced driver assistance system. The driver monitoring system is in communication with the advanced driver assistance system and includes a wearable device and a controller. The controller is programmed to provide a first signal to the wearable device responsive to the wearable device being within a predetermined distance from the vehicle.

According to another embodiment of the present disclosure, a driver monitoring system is provided. The driver monitoring system includes a wearable device and a controller. The wearable device is operable in a first mode and a second mode. The controller is programmed to provide a first signal to change the wearable device from the first mode to the second mode responsive to the wearable device being within a predetermined distance from a selectively autonomous vehicle.

According to yet another embodiment of the present disclosure, a method of monitoring a health condition of a driver of a vehicle is provided. The method includes activating a wearable device that is configured to provide a driver health signal and receiving the driver health signal at a controller. The method outputs for display a warning responsive to the driver health signal being indicative of at least one of an impending driver health event or current driver health event.

These and other advantages and features will become more apparent from the following description taken in conjunction with the drawings.

BRIEF DESCRIPTION OF THE DRAWINGS

The subject matter of the present disclosure is particularly pointed out and distinctly claimed in the claims at the conclusion of the specification. The foregoing and other features, and advantages of the present disclosure are apparent from the following detailed description taken in conjunction with the accompanying drawings in which:

DETAILED DESCRIPTION

Referring now to the Figures, where the present disclosure will be described with reference to specific embodiments, without limiting same, it is to be understood that the disclosed embodiments are merely illustrative of the present disclosure that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
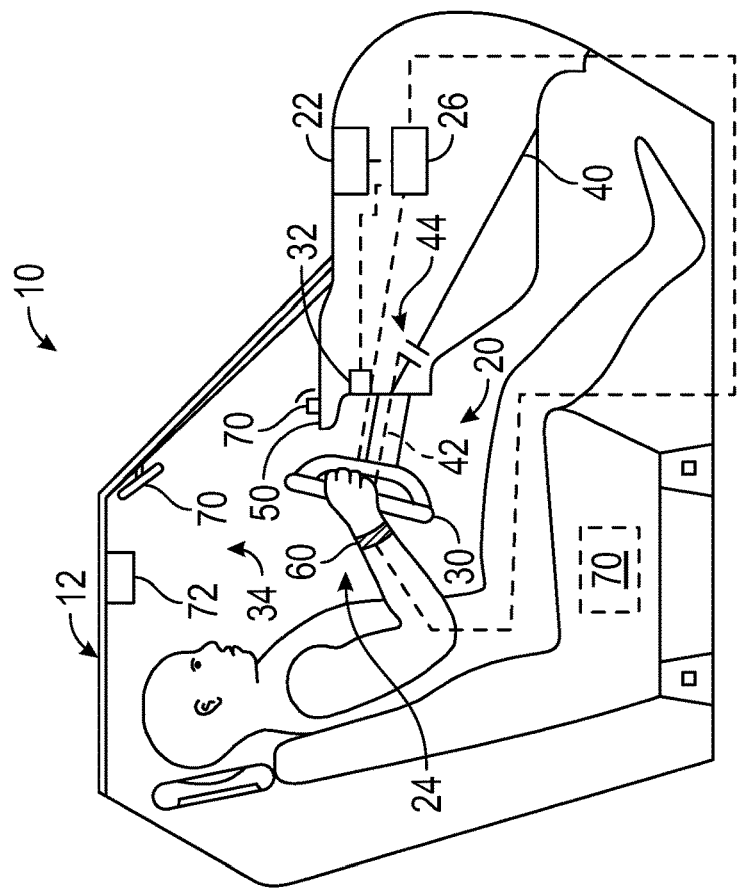
FIG. 1 is a schematic illustration of a vehicle compartment having a steering assembly in a retracted position.
Figure 2:
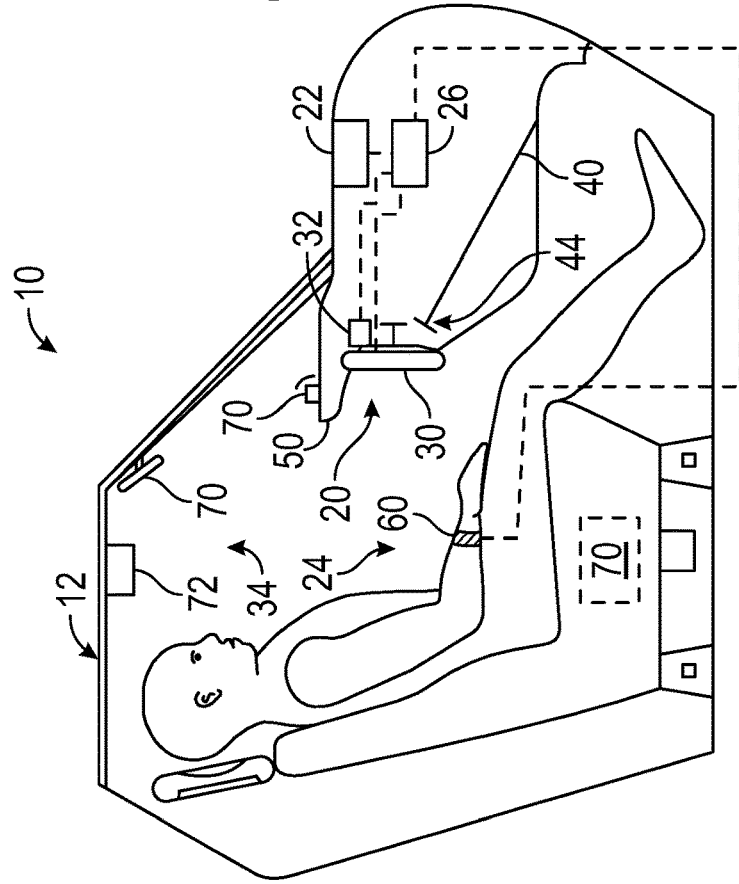
FIG. 2 is a schematic illustration of the vehicle compartment having a steering assembly in an deployed position.

Referring to FIGS. 1 and 2, a vehicle 10 may be a conventional vehicle, an autonomous vehicle, an autonomously driven vehicle, a selectively autonomous vehicle, or a vehicle having semi-autonomous capabilities. The vehicle 10 includes a steering assembly 20, an advanced driver assist system (ADAS) 22, and a driver monitoring system 24.

The steering assembly 20 is in communication with the ADAS 22, the driver monitoring system 24, and a controller 26 that may be provided as part of the driver monitoring system 24. The steering assembly 20 includes a steering wheel 30 and an adjustment assembly 32. The steering wheel 30 is selectively coupled to a steering shaft 40 that extends through a steering column along a steering column axis 42. The steering wheel 30 may be directly or indirectly coupled to the steering shaft 40 through a coupling mechanism 44.

The steering wheel 30 is coupled to the steering shaft 40 when the coupling mechanism 44 is at least partially engaged and the ADAS 22 is deactivated. The steering wheel 30 is decoupled from the steering shaft 40 when the coupling mechanism 44 is disengaged and the ADAS 22 is activated.

The steering wheel 30 of the steering assembly 20 is switchable between a rotating state/rotatable state and a non-rotating state/non-rotatable state. The steering wheel 30 is able to be rotated and the driver of the vehicle 10 is able to provide directional control of the vehicle 10 through the steering wheel 30 while the ADAS 22 is deactivated. The steering wheel 30 of the steering assembly 20 is in a non-rotating state, such that the steering wheel 30 is inhibited from rotating, while the ADAS 22 is activated. The steering wheel 30 is in the non-rotating state when the steering wheel 30 is operatively decoupled from the steering shaft 40. It is to be appreciated that decoupling the steering wheel 30 from the steering shaft 40 may be done mechanically, electrically, hydraulically, or a combination thereof.

The steering wheel 30 of the steering assembly 20 is movable between a retracted position, as shown in FIG. 1, and a deployed position by the adjustment assembly 32, as shown in FIG. 2, responsive to activation of the ADAS 22.

Referring to FIG. 1, the retracted position corresponds to a position in which the steering wheel 30 of the steering assembly 20 is disposed away from the driver and is disposed adjacent to or is received within an instrument panel 50. The retracted position provides increased space within the vehicle compartment 12 to enable the driver to perform non-driving activities. The ADAS 22 is actively controlling the vehicle 10 while the steering wheel 30 of the steering assembly 20 is in the retracted position and the ADAS 22 is activated. As the steering wheel 30 of the steering assembly 20 moves towards the retracted position or prior to the steering wheel 30 of the steering assembly 20 moving towards the retracted position, the steering wheel 30 may be operatively decoupled from the steering shaft 40.

Referring to FIG. 2, the deployed position corresponds to a driving position of the steering wheel 30 of the steering assembly 20 such that the steering wheel 30 accepts a driver input to provide directional control to the vehicle 10. The driver of the vehicle is actively controlling the vehicle 10 while the steering wheel 30 of the steering assembly 20 is in the deployed or extended position and the ADAS 22 is deactivated or in standby mode. As the steering wheel 30 of the steering assembly 20 moves towards the deployed position or as to the steering assembly 20 achieves the deployed position, the steering wheel 30 may be operatively coupled to the steering shaft 40.

The adjustment assembly 32 includes an actuator that is disposed proximate the steering column and is arranged to move the steering wheel 30 between the retracted position and the deployed position along the steering column axis 42. The actuator is at least one of an electronic actuator, a hydraulic actuator, a pneumatic actuator, or the like.

The adjustment assembly 32 is configured to move the steering wheel 30 from the retracted position towards the deployed position in response to a request to deactivate the ADAS 22. The adjustment assembly 32 is configured to move the steering wheel 30 from the deployed position towards the retracted position in response to a request to activate the ADAS 22.

The ADAS 22 is arranged to facilitate the performance of various vehicle operations (e.g. steering, accelerating, braking, maneuvering, etc.) without continuous input from a driver. The ADAS 22 is arranged to at least partially control the vehicle 10 while in an active state and does not at least partially control the vehicle 10 while in an inactive state. The ADAS 22 allows the vehicle 10 to be at least partially autonomously controlled using sensing, steering, and/or braking technology. A driver of the vehicle is able to selectively activate or deactivate the ADAS 22 via a switch or other mechanism.

The driver monitoring system 24 may be an automotive driver health monitoring and response system that is arranged to detect a driver health event and provide a warning or response to mitigate risks associated with the driver health event. The driver monitoring system 24 may identify a driver's state, a driver's behavior, a driver's health condition, and/or a change in the driver's state, the driver's behavior, and/or the driver's health condition. The driver monitoring system 24 is configured to identify a condition in which the driver may be unable to operate the vehicle 10 and may utilize the ADAS 22 to maneuver the vehicle to inhibit an accident or even guide the vehicle 10 towards a location. For example, the driver monitoring system 24 is arranged to monitor certain health conditions such as a seizure, syncope, an abnormal heart rhythm, sleep disorders, sleep apnea, narcolepsy, changes in blood pressure, body temperature, as well as other health conditions.

The driver monitoring system 24 is in communication with the ADAS 22 and the controller 26. The driver monitoring system 24 may include the controller 26 and a wearable device 60 that may be worn by a driver and includes a set of sensors such as a bio-signal sensor that may detect a biological signal (bio-signal) of the driver. The wearable device 60 measures or monitors a driver's state, health condition, and/or behavior. The collected information or data is sent to the controller 26 or a controller associated with another vehicle system and determines whether there is an impending or current driver health event. As used herein, the term "wearable" is understood to mean that the device may be worn by the driver as a watch, a bracelet, a necklace, a chest strap, an arm cuff, a patch, a headband, an ankle monitor, a belt, an ear clip, a helmet, a necklace, a device embedded into a vehicle seat, or may be incorporated into a vehicle seat belt. Regardless, the wearable device 60 is in direct contact with the driver's body such that the bio signal sensor may monitor or measure or track a bio signal.

The bio-signal sensor may monitor, measure, or track a bio-signal, such as, a driver's heart rate, a driver's blood pressure, a driver's blood sugar, a driver's oxygen saturation level (SpO2), a driver's respiration rate, a driver's heart rate/pulse rate, a driver's galvanic skin response (GSR), driver's body movements, or driver alertness. The bio-signal sensor may be an electrocardiogram (ECG), an electromyogram (EMG), a photoplethysmogram PPG, an electroneurogram (ENG), an electroencephalogram (EEG), a motion sensor, an accelerometer, a thermal sensor, or a thermometer. In at least one embodiment, the bio signal sensor may be configured to perform basic medical tests.

The wearable device 60 is in communication with the controller 26. The wearable device 60 may be in communication with the controller 26 through a wired connection, a wireless connection, near field communication, optical communication, or the like. The wearable device 60 is arranged to provide a driver health signal to the controller 26 and receive various signals from the controller 26. The driver health signal is a signal based on the bio signal that is indicative of the health condition or health state of the driver of the vehicle 10.

The first mode may be a low power mode in which the bio-signal sensor of the wearable device 60 does not monitor a bio-signal of the driver or the wearable device 60 does not provide or is inhibited from providing the driver health signal to the controller 26. The wearable device 60 may perform diagnostics and verify the functionality of the bio signal sensor while in the first mode. Should the wearable device 60 detect a fault with the bio signal sensor, the wearable device 60 may be disabled and may output an indicator for display indicative of the fault to the driver via a display of the wearable device 60 or via a display within the vehicle 10.

The second mode may be a mode in which the wearable device 60 is enabled to provide the driver health signal to the controller 26. The wearable device 60 may change from the first mode to the second mode responsive to the wearable device 60 being within a predetermined distance from the vehicle 10 or being within the vehicle compartment 12 of the vehicle 10.

Referring to FIGS. 1 and 2, the environmental detection system 34 is in communication with the ADAS 22, the controller 26, and the wearable device 60 of the driver monitoring system 24. The environmental detection system 34 is configured to monitor conditions within the vehicle compartment 12 that may impact the activation or deactivation of the ADAS 22, the retraction or extension of the steering wheel 30, or the state of the driver of the vehicle 10.

The environmental detection system 34 includes a cabin environmental sensor 70 and an output device 72. The cabin environmental sensor 70 provides a cabin environmental signal to the controller 26. The cabin environmental signal provides information indicative of at least one of the following conditions: an obstacle within a path of travel of the steering wheel 30, a location of the driver relative to the cabin environmental sensor 70, an availability or unavailability of the driver (e.g. the driver asleep, inattentive, or unavailable while in the driver's seat, the driver not within the driver's seat, an object in the driver's lap, etc.).

The cabin environmental sensor 70 may be disposed within the vehicle compartment 12. For example, the cabin environmental sensor 70 may be disposed on or within the instrument panel 50, disposed within or proximate the driver's seat, or disposed above the steering assembly 20. The cabin environmental sensor 70 may be at least one of a weight switch/sensor, an optical sensor, an ultrasonic sensor, a seatback sensor, a thermal sensor, and a biometric sensor configured to detect a heartbeat or respiration of the driver of the selectively autonomous vehicle.

The output device 72 is configured to output for display an indicator such as a visual, a haptic, or an audible indicator in response to the driver health signal being indicative of at least one of an impending driver health event or current driver health event and/or the cabin environmental signal providing information indicative of the following conditions: an obstacle between the steering wheel 30 and the driver, an object within a path of travel of the steering wheel 30, a location of the driver, and unavailable driver (e.g. the driver asleep within the driver's seat. The indicator provides a notification to the driver as to the situation within the vehicle compartment 12.

The controller 26 is in communication with the steering assembly 20, the ADAS 22, and the driver monitoring system 24. In at least one embodiment, the controller 26 is integrated with or provided as part of the driver monitoring system 24 or the ADAS 22.

The controller 26 includes input communication channels that are arranged to receive the driver health signal from the wearable device 60, a signal indicative of the state of the ADAS 22, and a signal indicative of the position of the steering wheel 30 of the steering assembly 20. The controller 26 includes output communication channels that are arranged to provide the first signal to the wearable device 60 to change the mode of the wearable device 60, a second signal to change the state of the ADAS 22, a signal to the output device 72, and a signal or message containing information indicative of the driver's health or driver's condition to a third-party or to a third-party device.

The controller 26 may include at least one microprocessor or central processing unit (CPU) in communication with various types of computer readable storage devices or media. Computer readable storage devices or media may include volatile and nonvolatile storage in read-only memory (ROM), random-access memory (RAM), and keep-alive memory (KAM), for example. KAM is a persistent or non-volatile memory that may be used to store various operating variables while the CPU is powered down. Computer-readable storage devices or media may be implemented using any of a number of known memory devices such as PROMs (programmable read-only memory), EPROMs (electrically PROM), EEPROMs (electrically erasable PROM), flash memory, or any other electric, magnetic, optical, or combination memory devices capable of storing data, some of which represent executable instructions, used by the controller 26.

The controller 26 is programmed to provide the first signal to the wearable device 60 responsive to the wearable device 60 being within a predetermined distance from the vehicle 10. As stated previously, the first signal may change the wearable device 60 from the first mode to the second mode. The wearable device 60 provides the driver health signal to the controller 26, in response to the wearable device 60 receiving the first signal. The wearable device 60 may continuously provide the driver health signal to the controller 26 and the controller 26 processes the driver health signal to determine whether there is an impending or existing driver health event regardless of the position of the steering wheel 30 of the steering assembly 20 and regardless of the state of the ADAS 22. However, the detection or determination of an impending or current driver health event by the controller 26 based on the driver health signal enables the controller 26 to change the position of the steering wheel 30 of the steering assembly 20 and/or change the state of the ADAS 22.

The controller 26 is programmed to provide the second signal to the ADAS 22 to change the state of the ADAS 22 from an inactive state to an active state responsive to the driver health signal of the wearable device 60 being indicative of at least one of an impending driver health event or current driver health event, should the ADAS 22 be in an inactive state.

The controller 26 is programmed to output for display a warning indicative of the at least one of an impending or current driver health event responsive to the driver health signal being indicative of at least one of an impending driver health event or current driver health event. The warning may be output for display by the output device 72 and may alert the driver of the vehicle 10 as to the impending or current driver health event.

The controller 26 is programmed to command the ADAS 22 to operate the vehicle 10 to follow an event selected autonomous path. The event selected autonomous path is based on at least one of the impending driver health event or current driver health event. The event selected autonomous path may be a vehicle path or course to the nearest or most accessible emergency facility, a predetermined location, towards the side of the road, or other preprogrammed locations capable of enabling a response to the impending driver health event or the current driver health event. Furthermore, the controller 26 may inhibit the driver the vehicle 10 from entering into a manual mode, in which the driver may provide steering inputs to the vehicle 10, or inhibit the driver the vehicle 10 from moving the steering wheel 30 of the steering assembly 20 from the retracted position towards the deployed position to initiate a handover of vehicle control to the driver the vehicle 10.

For example, should the impending driver health event or the current driver health event have a severity less than a threshold, such that the driver of the vehicle 10 may be able or available to regain control of the vehicle 10, the controller 26 may command the ADAS 22 to direct the vehicle 10 towards the side of the road or to a predetermined safe location. Should the impending driver health event or the current driver health event have a severity greater than a threshold, such that the driver of the vehicle 10 may be unable or unavailable to regain control the vehicle 10, the controller may command the ADAS 22 to direct or guide the vehicle 10 towards an emergency or ambulatory facility.

In at least one embodiment, the controller 26 is programmed to contact the emergency facility and transmit a signal or message containing information indicative of the driver's health or driver's condition to the emergency facility or to a third-party device. The controller 26 may be programmed to make secured, recorded driver health information available to authorized medical service providers and other authorized units using secure media.

In at least one embodiment, the controller 26 is programmed to inform another vehicle through vehicle to vehicle communication (V2V) or is programmed to inform vehicle to infrastructure communication (V2X) for safer and faster execution of the vehicle 10 traversing the event selected autonomous path.

The controller 26 is programmed to command the ADAS 22 to operate the vehicle 10 to follow an event selected autonomous path responsive to the driver health signal provided by the wearable device 60 being indicative of at least one of an impending driver health event or current driver health event, should the steering wheel 30 of the steering assembly 20 be in the retracted position and the ADAS 22 be in an active state.

Figure 3:
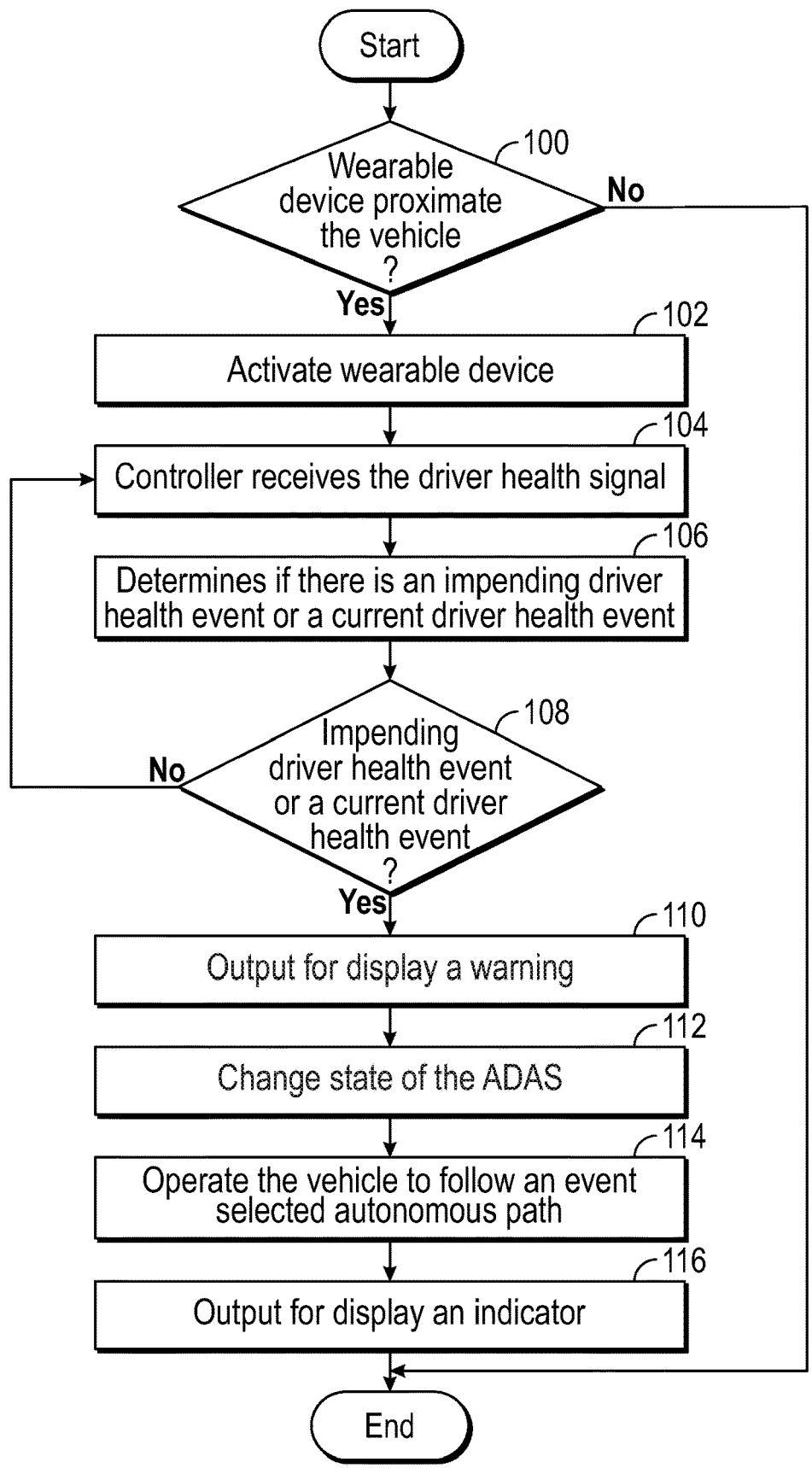
FIG. 3 is a flowchart of an illustrative method of monitoring a health condition of a driver of the vehicle.

Referring to FIG. 3, a flowchart of an illustrative method of monitoring a health condition of the driver of the vehicle is shown. As will be appreciated by one of ordinary skill in the art, the flowchart represents control logic that may be implemented or affected in hardware, software or combination of hardware and software by the controller 26.

At block 100, the method may detect the presence of a driver wearing the wearable device 60 proximate the vehicle 10. If the driver wearing the wearable device 60 is not within a predetermined distance or within the vehicle 10, the method may end at block 120. Should the driver wearing the wearable device 60 be within the vehicle compartment 12 or within a predetermined distance of the vehicle 10, the method may continue to block 102.

At block 102, the wearable device 60 is activated or changed from a first mode to a second mode and provides a driver health signal to the controller 26. At block 104, the controller 26 receives the driver health signal. At block 106, the controller 26 provides the driver health signal to a processor that determines if there is an impending driver health event or a current driver health event based on information or data provided by the driver health signal.

At block 108, the method determines if there is an impending driver health event or a current driver health event. If there is not an impending driver health event or a current driver health event, the method may return to block 104 where the method continues to receive the driver health signal from the wearable device 60. Should there be an impending driver health event or a current driver health event, the method may continue to block 110.

At block 110, the method may output for display a warning. The warning may be output by the output device 72 to alert the driver of the vehicle 10 of the impending driver health event or the current driver health event. The method then continues to block 112. In the case of a conventional vehicle that is not an autonomous vehicle or is not a selectively autonomous vehicle and incorporates the driver monitoring system 24, responsive to the impending driver health event or a current driver health event, the method may output a warning and the method may continue to block 116 or may end.

At block 112, the method changes a state of the ADAS 22 from the inactive state (e.g. a manual vehicle mode or driver controlled mode) to an active state (e.g. an autonomous vehicle mode or partially autonomous mode), should the ADAS 22 be in an inactive state. Should the ADAS 22 be in the active state and the vehicle 10 is being operated to follow a driver selected path, the method changes a vehicle path from the driver selected path to an event selected autonomous path. The method then continues to block 114.

At block 114, the method operates the vehicle 10 to follow an event selected autonomous path based on the impending driver health event or the current driver health event. The method then continues to block 116.

At block 116, the method outputs for display an indicator indicative of at least one of an impending driver health event or a current driver health event to a third party or to a third party device. The method may then end at block 120.

While the present disclosure has been described in detail in connection with only a limited number of embodiments, it should be readily understood that the present disclosure is not limited to such disclosed embodiments. Rather, the present disclosure can be modified to incorporate any number of variations, alterations, substitutions or equivalent arrangements not heretofore described, but which are commensurate with the scope of the present disclosure. Additionally, while various embodiments of the present disclosure have been described, it is to be understood that aspects of the present disclosure may include only some of the described embodiments or combinations of the various embodiments. Accordingly, the present disclosure is not to be seen as limited by the foregoing description.

Having thus described the invention, it is claimed:

1. A steering assembly, comprising:
   an advanced driver assistance system (ADAS) arranged to control the steering assembly;
   a steering wheel movable between a deployed position and a retracted position based on a state of the ADAS, the steering wheel switchable between a rotatable state and a non-rotatable state based on a state of the ADAS;
   a driver monitoring system in communication with the ADAS, the driver monitoring system comprising:
      a wearable device including a sensor for direct contact with a driver's body to monitor a driver health condition, and
      a controller programmed to provide a first signal to the wearable device responsive to the wearable device being within a predetermined distance from the steering assembly, the controller being further programmed to command the ADAS to operate the steering assembly to follow an event selected autonomous path, the event selected autonomous path being based on a detection of the driver health condition being one of an impending driver health event or a current driver health event; and
   an environmental detection system in communication with the ADAS and the driver monitoring system.

2. The steering assembly of claim 1, wherein the wearable device is arranged to provide a driver health signal reflective of the monitored driver health condition to the controller responsive to receipt of the first signal.

3. The steering assembly of claim 2, wherein the controller is further programmed to change the state of the ADAS responsive to the driver health signal being indicative of the impending driver health event or the current driver health event.

4. The steering assembly of claim 2, wherein the controller is further programmed to, while the ADAS is in an inactive state and responsive to the driver health signal being indicative of at least one of the impending driver health event or the current driver health event, output for display a warning indicative of at least one of an impending or current driver health event.

5. The steering assembly of claim 4, wherein the controller is further programmed to change the ADAS from the inactive state to an active state responsive to the detection of the impending driver health event or the current driver health event.

6. The steering assembly of claim 4, wherein the event selected autonomous path is a vehicle path to a predetermined location.

7. The steering assembly of claim 6, wherein the predetermined location is a medical facility selected to correspond to the impending driver health event or the current driver health event.

8. The steering assembly of claim 2, wherein the sensor is a bio signal sensor to execute one or more medical tests.

9. A driver monitoring system, comprising:
a steering wheel movable between a deployed position and a retracted position, the steering wheel switchable between a rotatable state and a non-rotatable state;
a wearable device operable in a first mode and a second mode and including a sensor for direct contact with a driver's body to identify a driver health condition,
an output device disposed within a vehicle; and
a controller in communication with the steering wheel, the wearable device, and the output device, the controller being programmed to provide a first signal to the wearable device to change the wearable device from the first mode to the second mode responsive to the wearable device being within a predetermined distance from the vehicle and the controller being further programmed to direct the vehicle to follow an event selected autonomous path responsive to the steering wheel being in the retracted position and the sensor identifying an impending driver health event or a current health event of the driver.

10. The driver monitoring system of claim 9, wherein while the wearable device is in the first mode, the wearable device is inhibited from providing a driver health signal to the controller and while the wearable device is in the second mode, the wearable device is enabled to provide a signal reflective of the driver's health to the controller.

11. The driver monitoring system of claim 10, wherein the controller is in communication with an advanced driver assistance system (ADAS) that at least partially controls the vehicle while in an active state and does not control the vehicle while in an inactive state.

12. The driver monitoring system of claim 11, wherein the controller is further programmed to, while the ADAS is in the inactive state and responsive to the driver health signal being indicative of at least one of the impending driver health event or the current driver health event, change the ADAS from the inactive state to the active state.

13. The driver monitoring system of claim 11, wherein the controller is programmed to, responsive to the driver health signal being indicative of at least one of the impending driver health event or the current driver health event, output for display a warning indicative of the driver health signal.

14. The driver monitoring system of claim 10, wherein the output device is configured to output for display an indicator, responsive to the driver health signal being indicative of at least one of the impending driver health event or the current health event.

15. The steering assembly of claim 2, wherein the environmental detection system includes:
a cabin environmental sensor arranged to provide a cabin environmental signal indicative of at least one of a location of a driver relative to the cabin environmental sensor and an availability of the driver to the controller; and
an output device configured to output for display an indicator responsive to at least one of the cabin environmental signal of an unavailable driver and the driver health signal being indicative of at least one of the impending driver health event or the current driver health event.

* * * * *